US007858332B2

(12) United States Patent
Mutter et al.

(10) Patent No.: US 7,858,332 B2
(45) Date of Patent: Dec. 28, 2010

(54) CHEMOPREVENTION OF ENDOMETRIAL CANCER

(75) Inventors: George Mutter, Chestnut Hill, MA (US); Akila Viswanathan, Cambridge, MA (US); Anne Ørbo, Tromso (NO)

(73) Assignees: The Brigham and Women's Hospital, Inc., Boston, MA (US); University of Tromsø, Tromsø (NO)

( * ) Notice: Subject to any disclaimer, the term of this patent is extended or adjusted under 35 U.S.C. 154(b) by 618 days.

(21) Appl. No.: 11/655,895

(22) Filed: Jan. 22, 2007

(65) Prior Publication Data
US 2007/0212392 A1    Sep. 13, 2007

Related U.S. Application Data

(60) Provisional application No. 60/762,515, filed on Jan. 27, 2006.

(51) Int. Cl.
*G01N 33/53* (2006.01)
(52) U.S. Cl. .................................. 435/7.23; 424/198.1
(58) Field of Classification Search .................. None
See application file for complete search history.

(56) References Cited

U.S. PATENT DOCUMENTS

| | | | |
|---|---|---|---|
| 3,935,860 A | 2/1976 | Hoff | |
| 3,993,057 A | 11/1976 | Ramwell | |
| 4,014,987 A | 3/1977 | Heller | |
| 4,016,251 A | 4/1977 | Higuchi | |
| 4,188,951 A | 2/1980 | Higuchi | |
| 4,344,431 A | 8/1982 | Yolles | |
| 4,431,548 A | 2/1984 | Lipowski | |
| 4,578,076 A | 3/1986 | Luukkainen | |
| 5,626,148 A | 5/1997 | Lehtinen | |
| 6,482,407 B2 * | 11/2002 | Soo Hoo | 424/93.21 |
| 6,649,259 B1 | 11/2003 | Hu | |
| 6,649,359 B2 | 11/2003 | Mutter | |

OTHER PUBLICATIONS

Kim et al. (Cancer, vol. 79(2), pp. 320-327, 1997).*
International Search Report for PCT/US 2007/01749 filed Jan. 23, 2007.
Written Opinion of the International Searching Authority for PCT/US 2007/01749 filed Jan. 23, 2007.
Apgar, et al., "Using Progestins in Clinical Practice," *American Family Physician* 62:1839-1849 (Oct. 2000).
Baak, et al., "EIN and WH094: Considering the Classification of Endometrial Hyperplasia," *J. Clin. Pathol.* 58:1-6 (2005).
Benshushan, et al., "IUD Use and the Risk of Endometrial Cancer," *Eur. J. Obstet. Gynecol. Reprod. Biol.* 105(2):166-169 (2002).
Hecht, et al., "Prediction of Endometrial Carcinoma by Subjective Endometrial Intraepithelial Neoplasia Diagnosis," *Mod. Pathol.* 18:324-330 (2005).
Hill, et al., "Endometrial Cancer in Relation to Intra-Uterine Device Use," *Int. J. Cancer* 70:278-281 (1997).

Montz, et al., "Intrauterine Progesterone Treatment of Early Endometrial Cancer," *Am. J. Obstet. Gynecol.* 186(4):651-657 (Apr. 2002).
Mutter, et al., "Altered PTEN Expression as a Diagnostic Marker for the Earliest Endometrial Precancers," *J. Natl. Cancer Inst.* 92(11):924-930 (Jun. 2000).
Mutter, et al., "Molecular Identification of Latent Precancers in Histologically Normal Endometrium," *Cancer Res.* 61:4311-4314 (Jun. 2001).
Mutter, et al., "PTEN, a Protean Tumor Suppressor," *Am. J. Pathol.* 158(6):1895-1898 (Jun. 2001).
Mutter, et al., "Endometrial Precancer Diagnosis by Histopathology, Clonal Analysis, and Computerized Morphometry," *J. Pathol.* 190:462-469 (2000).
Mutter, et al., "Changes in Endometrial PTEN Expression Throughout the Human Menstrual Cycle," *J. Clin. Endocrinol. Metab.* 85:2334-2338 (2000).
Perino, et al., "Treatment of Endometrial Hyperplasia with Levonorgestrel Releasing Intrauterine Devices," *Acta. Eur. Fertil.* 18:137-140 (1987).
Rossouw, et al., "Risks and Benefits of Estrogen Plus Progestin in Healthy Postmenopausal Women," *JAMA* 288:321-333 (Jul. 2002).
Seppanen, Marjo, "Cytokines and Gynecological Cancer: In Vitro Effects on Ovarian, Endometrial and Vulvar Carcinoma Cells," *Acta Universitatis Tamperensis* 762 (Aug. 11, 2000).
Stambolic et al., "High Incidence of Breast and Endometrial Neoplasia Resembling Human Cowden Syndrome in pten +/– Mice," *Cancer Res.* 60:3605-3611 (Jul. 2000).
Vereide, et al., "Nuclear Morphometric Changes and Therapy Monitoring in Patients with Endometrial Hyperplasia: a Study Comparing Effects of Intrauterine Levonorgestrel and Systemic Medroxyprogesterone," *Gynecologic Oncology* 91:526-533 (2003).
Zheng, et al., "Involution of PTEN-Null Endometrial Glands with Progestin Therapy," *Gynecologic Oncology* 92:1008-1013 (2004).
International Preliminary Report on Patentability for PCT/US 2007/01749 filed Jan. 23, 2007.

* cited by examiner

*Primary Examiner*—Misook Yu
*Assistant Examiner*—Meera Natarajan
(74) *Attorney, Agent, or Firm*—Law Office of: Michael A. Sanzo, LLC

(57) ABSTRACT

The present invention is directed to intrauterine devices that release progestins or an inflammatory cytokine after placement. These devices can be used to reduce the risk of a woman developing endometrial cancer. The invention is also directed to therapeutic methods in which a sample of uterine cells obtained from a woman is assayed to determine the extent to which PTEN null clones (latent endometrial precancers) are present. In cases where the number of such null clones is high, the woman is administered an intrauterine device that releases either a progestin or an inflammatory cytokine.

20 Claims, No Drawings

CHEMOPREVENTION OF ENDOMETRIAL CANCER

CROSS REFERENCE TO RELATED APPLICATIONS

This application claims priority to, and the benefit of, U.S. provisional application No. 60/762,515, filed on Jan. 27, 2006, which is incorporated in its entirety herein by reference.

STATEMENT OF GOVERNMENT FUNDING

The United States Government has a paid-up license in this invention and the right in limited circumstances to require the patent owners to license others under reasonable terms as provided for by the terms of NIH Grant Nos. R01-CA100833 and R01-CA92301, awarded by the Department of Health and Human Services.

FIELD OF THE INVENTION

The present invention is directed to drug-releasing intrauterine devices that can be used in women identified as being at high risk of developing endometrial cancer. The devices may be impregnated with certain hormones or inflammatory substances (such as cytokines) and used in women who have preclinical neoplastic disease, such as those with histologically normal endometrium containing somatic mutations in the gene for the tumor cell suppressor PTEN (i.e., in women with "latent precancers").

BACKGROND OF THE INVENTION

Endometrial cancer originates in cells lining the uterus and is the fourth most common type of cancer found in women. It is estimated that there are about 35,000 new cases of endometrial cancer diagnosed each year in the United States, resulting in 4,000 to 5,000 deaths annually. The disease most typically occurs in postmenopausal women, with the average age at the time of diagnosis being about 60 years. Often, the development of endometrial cancer is preceded by premalignant neoplastic growth of endometrial glandular cells, a condition that is usually apparent upon histological examination (Hecht, et al., *Mod. Pathol* 18:324-330 (2005); Mutter et al., *J. Pathol* 190:462-469 (2000)) as atypical hyperplasia, or Endometrial Intraepithelial Neoplasia ("EIN"). Unfortunately, by the time that EIN is detected, cancer is already present in approximately 39% of women (Baak, et al., *J. Clin. Pathol.* 58:1-6 (2005)).

A change in the expression of a tumor cell suppressor protein, PTEN, is the most common genetic abnormality in endometrial cancer, and occurs before any other known clinical manifestations (Mutter, et al., *J. Nat'l Cancer Inst.* 92:924-30 (2000); U.S. Pat. No. 6,649,259). Histologically unremarkable clones of endometrial cells containing PTEN mutations (PTEN null clones, "Latent precancers") are believed to constitute latent precancers that, under the influence of estrogen hormones, preferentially proliferate (Mutter, et al., *Cancer Res.* 61:4311-4314 (2001); Mutter, et al., *J. Clin. Endocrinol. Metab.* 85:2334-2338 (2000)). Reducing the number of these cells should therefore also reduce the risk of women progressing to fully developed endometrial cancer (Zheng, et al, *Gynecol. Oncol* 92:1008-1013 (2004)).

Systemic administration of progestins is known to reduce both the risk of endometrial cancer and the number of PTEN null clones (latent precancers) (Zheng, et al., *Gynecol Oncol* 92:1008-13 (2004)). However systemic progestin has also been associated with an increased risk of stroke and heart attack, especially in women who smoke, and these factors have limited its clinical usefulness (PEPI Trial Report, *JAMA* 275:370-375 (1996); Rossouw, et al., *JAMA* 288:321-333 (2002)). Intrauterine devices (IUDs) impregnated with progestins (e.g., levonorgestrel) are also capable of reducing the risk of endometrial cancer in women with premalignant hyperplasias and have the advantage of delivering high local endometrial dosages with low systemic levels (Perino, et al., *Acta Eur. Fertil.* 18:137-140 (1987); Vereide, et al., *Gynecol Oncol* 91:526-533 (2003)). They therefore carry a much lower risk of causing serious extrauterine side effects. It has also been reported that certain inflammatory derived compounds, such as cytokines, have an inhibitory effect on growth of cancerous endometrial cells in vitro (Seppanen, Maijo, Cytokine and Gynecological Cancer. *In Vitro Effects of Cytokines on Ovarian, Endometrial and Vulvar Carcinoma Cells*, Acta Universitatis 762, Tempere University Press, ISBN 951-44-4883-9 (2000) (Dissertation)).

What has remained unclear is whether intrauterine treatments involving the use of IUDs impregnated with anticancer agents such as progestins and cytokines are advisable for use in women with latent precancers (PTEN mutant endometrial clones) who do not have hyperplasia. It has also been unclear whether IUD treatment can reverse latent precancers at a time when the presence of PTEN null clones is the only evidence of increased cancer risk.

The coupling of cancer susceptibility testing by latent precancer detection (using PTEN endometrial immunohistochemistry) with IUD delivery of anticancerous agents is of importance for two main reasons. First, some women at high risk may never exhibit premalignant lesions like EIN that are detectable by routine pathologic examination. If PTEN is used as a marker in combination with IUD treatment, the number of these women that progress to cancer could be reduced with a much lower risk of stroke or heart attack than if systemic progestins were given in unselected patients. Second, this presents an effective cancer prevention strategy by detecting and treating latent precancers before they would normally be diagnosed, thereby further decreasing the likelihood of cancer arising.

SUMMARY OF THE INVENTION

The present invention is based upon the discovery that intrauterine devices (IUDs), particularly those impregnated with agents shown to reduce the risk of cancer development (e.g., progestins and cytokines), promote the elimination of "latent precancerous cells" in the uterus of women. Latent precancerous cells are characterized by histologically unremarkable endometrial tissues in which the affected glands lack activity associated with the tumor cell suppressor PTEN, in most cases due to mutations or deletion of the PTEN gene (see Examples section below). These are quite common, being present in 43% of naturally cycling premenopausal women (Mutter, et al., *Cancer Res.* 61:4311-4314 (2001))

In its first aspect, the invention is directed to a method for reducing the risk of a woman developing endometrial cancer by coupling IUD placement with qualifying PTEN assays. The method involves obtaining a test sample of uterine endometrial cells from a woman and determining the level of PTEN expression or activity present, e.g., using immunohistochemistry or a similar technique (see U.S. Pat. No. 6,649,359, the contents of which are hereby incorporated by reference). A comparison is then made between the levels determined in endometrial glands and those present in one or more comparison control samples. Controls may include internal controls of endometrial stromal tissue, a comparison of gland subsets within one sample, or external controls of comparison with separate endometrial specimens. In cases where the test sample PTEN level is lower than that observed in the control samples, a PTEN-null clone or latent precancer, is determined to be present and the woman is implanted with an IUD. This method should be effective in women that, apart from abnormal PTEN expression, do not have any overt clinical indications that they are at increased risk of developing endometrial cancer, e.g., women that do not have a history of endometrial cancer and whose uterus does not exhibit EIN or glandular hyperplasia.

The IUD implanted should, preferably, release an anticancer substance, e.g., a progestin or inflammatory mediator such as a cytokine, into the uterus of the woman. Any type of progesterone or progestin that has been described in the art may be used in the IUD including: progesterone itself; acetoxypregnenolone; anagestone acetate; chlormadinone acetate; desogestrol; dimethisterone; ethisterone; ethynodiol diacetate; fluorogestone acetate; gestodene; hydroxymethylprogesterone; hydroxymethylprogesterone acetate; hydroxyprogesterone; hydroxyprogesterone acetate; hydroxyprogesterone caproate; levonorgestrel; lynestenol; medroxyprogesterone; melengestrol acetate; norethindrone; norethindrone acetate; norgesterol; normethisterone; and pregnenolone. In addition, it will be understood that any pharmaceutically acceptable form of these compounds may be used in the invention, i.e., different salt forms may be employed. Examples of IUDs already on the market that release progestins and which could be used are Progestasert™ (manufactured by Alza Corp., Palo Alto, Calif., releasing progesterone), and Mirena™ (manufactured by Berlex Inc., Montville, N.J., releasing levonorgestrel). One advantage of using IUDs to release progestin is that, due to localized delivery, much lower doses can be used than what would be necessary if delivery was systemic. In general, the IUDs should be designed to release 1-100 micrograms, and preferably 5-50 micrograms, of progesterone or progestin in a 24-hour period. Sufficient progestin should be included in the IUD so that replacement is not necessary for at least a period of one year and, preferably, not for a period of at least five years.

Inflammatory cytokines that may be released by IUDs include: interleukin-1(IL-1); interleukin-6 (IL-6); interleukin-11 (IL-11); tumor necrosis factor-alpha (TNF-α); tumor necrosis factor-beta (TNF-β); interferon-alpha (IFN-α); interferon-beta (IFN-β); interferon-gamma (IFN-γ); leukemia inhibitory factor (LIF); oncostatin M (OSM); ciliary neurotrophic factor (CNTF); interleukin-8 (IL-8); interleukin-12 (IL-12); platelet factor-4 (PF-4); platelet basic protein (PBP); neutrophil activating protein-2 (NAP-2); beta-thromboglobulin (β-TG); macrophage inflammatory protein-1alpha (MIP-1α); macrophage inflammatory protein-1beta (MIP-1β); monocyte chemoattractant protein-1 (MCP-1); monocyte chemoattractant protein-2 (MCP-2); monocyte chemoattractant protein-3 (MCP-3); regulated upon activation normal T expressed and presumably secreted cytokine (RANTES); and lymphotactin. The most preferred of these cytokines are IL-6 and TNF-α. In general, the cytokines should be released in an amount of 0.01-100 micrograms (and preferably 0.1-50 micrograms) over a 24-hour period. Sufficient cytokine should be included in an implanted IUD to maintain an effective dosage for a period of at least one year after placement and, preferably, for a period of at least five years.

In the case of IUDs releasing progestins or cytokines, women at risk for developing endometrial cancer may be identified based upon a family history of the disease, a prior episode of endometrial cancer, EIN or atypical hyperplasia in the uterus, or the presence of latent precancers documented by abnormal levels of PTEN. The most preferred method is by performing PTEN assays as discussed above. Regardless of the way in which women are identified, the same preferred progestins, inflammatory cytokines and dosages discussed above should be employed.

In another aspect, the invention is directed to an IUD which is designed to release one or more inflammatory cytokines and which is suitable for use in the methods described above. Any of the various drug-releasing IUDs that have been described in the art may be used in connection with cytokine release, including the types of commercially available devices described above. Examples of inflammatory cytokines that may be used include: IL-1; IL-6; IL-11; TNF-α; TNF-β; IFN-α; IFN-β; IFN-γ; LIF; OSM; CNTF; IL-8; IL-12; PF4; PBP; NAP-2; β-TG; MIP-1α; MIP-1β; MCP-1; MCP-2; MCP-3; RANTES; and lymphotactin. Of these, the most preferred are IL-6 and TNF-α. The devices should be designed to release between 0.01 and 100 micrograms (and, preferably, 0.1-50 micrograms) of inflammatory cytokine over a 24-hour period. In addition, they should contain a total amount of inflammatory cytokine sufficient to maintain an effective dosage for a period of at least one year and, preferably, five years. Thus, there will generally be 0.05-500 mg of inflammatory cytokine and, preferably, 0.05-50 mg of inflammatory cytokine, present in total.

DESCRIPTION OF THE INVENTION

A. PTEN Assays

Assays for determining PTEN levels, and detection of latent endometrial precancers, in a sample of uterine endometrial cells obtained from a patient and the value of these assays in assessing the risk of a woman developing endometrial cancer have been previously described (U.S. Pat. No. 6,649,359; Mutter, et al., *J. Nat. Cancer Inst.* 92:924-931(2000); Mutter, et al., *Cancer Res.* 61:4311-4314 (2001)). The teachings of these references are hereby incorporated by reference in their entirety. In general, the most useful of these assays are based either upon immunohistochemical staining or PCR amplifications (see U.S. Pat. No. 6,649,359). Immunohistochemical methods utilize commercially available antibodies against PTEN, e.g., monoclonal antibody 6h2.1 (Cascade Biosciences), polyclonal rabbit anti-PTEN, MMAC1 (Zymed, PCS-Biologicals); PTEN clone A2b1 Hu Ms monoclonal (Chemicon); PTEN N-19 and A2b1 (Santa Cruz Biotechnology); PTEN C terminus polyclonal rabbit anti-PTEN (Zymed); PTEN mouse anti-human monoclonal AB-1 (Calbiochem, Clone 6B1); and PTEN mouse anti-human monoclonal AB-2 (Calbiochem, Clone 1A7). These antibodies may be detectably labeled and used for staining using standard techniques. Alternatively, as discussed in U.S. Pat. No. 6,649,359, PCR amplification may be performed to determine the extent to which PTEN RNA is being expressed and whether DNA mutations are present.

Any other technique for assessing PTEN levels or activity in a uterine sample of endometrial cells should also be compatible with the present invention. The most critical factor is to determine the extent to which expression or activity in the test sample compares with that present in controls, typically unaffected endometrial glands or stroma elsewhere in the test biopsy, or tissue samples from women that do not have any characteristics suggesting they are at increased risk for developing endometrial cancer, e.g., a history of endometrial cancer, EIN, or endometrial hyperplasia. The more that test samples evidence a relative reduction in the expression of active PTEN (or a greater number of null glands, i.e., PTEN non-expressing clones), the greater risk of endometrial cell cancer arising.

B. Manufacture and Use of Intrauterine Devices

IUDs have been on the market since at least the 1970s and many different methods have been described for manufacturing ordinary IUDs (see U.S. Pat. No. 3,935,860) and drug-releasing IUDs (see U.S. Pat. Nos. 4,014,987; 3,993,057; 4,016,251; 4,188,951; 4,344,431; 4,578,076; and 5,626,148). Any of the designs described in the art are compatible with the present invention and the references describing IUD manufacture are hereby incorporated by reference in their entirety. Three IUDs that are presently on the market which release progestin and which provide an example of the type of device that may be used in connection with the present invention are Mirena™, (manufactured by Berlex Inc., Montville, N.J. and releasing levonorgestrel), Levonova device (releasing 20 micrograms of levonorgestrel per day, Schering, Turku, Finland) and Progestasert™ (manufactured by Alza Corp. (Palo Alto, Calif. and releasing progesterone). Studies have indicated that certain progestin-releasing IUDs may be effective in the treatment of patients with endometrial hyperplasia (see, e.g., Vereidy, et al, *Gynecologic Oncol.* 91:526-533 (2003)).

The IUDs of the present invention may be designed to deliver much lower concentrations of progestin than many of those described in the prior art and, in general, should release between about 1 and 100 micrograms of progestin over a 24-hour period. For the purposes of the present invention, a "progestin" is considered to be any drug that binds to the progestin receptor and induces a progestational effect. This includes all of the known progestins, derivatives of progesterone or testosterone that have progestin activity, and progestin agonists. The known synthetic progestins are mainly derivatives of 17-alphahydroxy-progesterone or 19-nortestosterone. These progestins are often classified into three groups: pregnane, estrange and gonane derivatives, all of which are compatible with the present invention and may be manufactured using techniques that are well known in the art. Many are commercially available and oral drug preparations are on the market for norgestrel, medroxyprogesterone acetate, norethindrone and norethindrone acetate. Although any of these compounds may be used with the present invention, the most preferred progestin is levonorgestrel.

Another group of compounds that may be released by IUDs instead of progestins are inflammatory cytokines. In vitro studies have indicated that these compounds are effective against cancerous endometrial cells (see Seppanen, *Cytokines and Gynecological Cancer. In Vitro Effects of Cytokines on Ovarian Endometrial and Vulvar Carcinoma Cells*, Tampere University Press, ISBN 951-44-4883-9 (Dissertation)). While not being held to any particular mechanism of action, it is believed that the observed ability of IUDs to reduce the risk of endometrial cancer may be due to their inducing inflammatory or repair processes that negatively select for latent precancer clones, thereby causing their involution. The placement of an inert intrauterine device initiates a series of local changes that increase endometrial concentrations of certain inflammatory cytokines, such as interleukin-6 and tumor necrosis factors-α (see Archer, et al. (*Contraception* 59:175-179 (1999)). Devices that release cytokines may be made by the processes described in the above-cited references and should, in general, release between 0.01 and 100 micrograms of inflammatory cytokine over a 24-hour period. Methods for making inflammatory cytokines are well known in the art and many are commercially available. The ones most preferred for use in the present invention are IL-6 and TNF-α.

C. Treatment Methods

Any of the methods known in the art for implanting IUDs may be used in connection with the present invention. Placement should, preferably, take place as soon after a woman has been identified as being at increased risk of developing endometrial cancer as possible. Indications of increased risk are: a family history of endometrial cancer; a prior endometrial cancer episode; uterine endometrial cell hyperplasia; and/or abnormal levels of uterine PTEN. The PTEN assays that have been described in the art are the most preferred method since these provide the earliest indication of elevated risk.

After IUD placement has occurred, the effectiveness of the treatment may be followed by obtaining subsequent samples of uterine endometrial cells over a period of weeks or months and performing PTEN assays on each sample. Successful treatment should be evidenced by an increase in overall PTEN levels and/or a decrease in the number of PTEN null clones. If the results of the follow-up assays indicate that the IUD is not effectively reducing cancer risk, then the dosage of IUD-released active agent may be adjusted or an IUD releasing a different agent may be employed. For example, if a woman has been treated using an IUD releasing a progestin, an IUD releasing an inflammatory cytokine may be used in its place or, alternatively, both a cytokine and a progestin may be released, e.g., by implanting two IUDs or by implanting a single IUD designed to release both agents. IUDs releasing other types of agents for the prevention of cancer may also be used either alone or in conjunction with other agents or other IUDs. In general, it will be desirable to have more than one type of IUD available, both with respect to the dosage of active agent released and the type of active agent released.

Although the dosages suggested herein may be used for guidance, the skilled practitioner will make adjustments on a case-by-case basis, using methods that are well established in the art of clinical medicine. The invention is also compatible with the release of agents or excipients from IUDs in addition to the active agents discussed above. In this regard, guidance concerning appropriate buffers or excipients may be found in standard works in the art, such as *Remington's Pharmaceutical Sciences*, (16$^{th}$ ed. A. Oslo, Easton, Pa. (1980)).

EXAMPLES

The present examples present data in support of the efficacy of IUDs causing the involution of latent endometrial precancers as detected by PTEN immunohistochemistry. In Example 1, we show a reduction of latent endometrial precancers using IUDs made of inert materials, and propose that these IUDs exert their effect through local cytokine mediated inflammatory responses. In Example 2, we show involution of latent endometrial precancers identified by PTEN immunohistochemistry through placement of progestin impregnated IUDs. Combined, these data show feasibility and efficacy of the proposed methods in the therapy of latent phases of endometrial cancer.

Example 1

Latent PTEN-null Endometrial Clones are Reduced in Women Treated with Inert Intrauterine Devices (Inert-IUD)

Table1 shows the prevalence of women with PTEN-null glands in (inert) IUD exposed and age-matched control endometria studied at Brigham and Women's hospital in Boston. Patients were selected by tissue availability and lack of recent therapeutic hormonal use, and endometrial specimens underwent PTEN immunohistochemistry using monoclonal antibody 6h2.1 according to detailed Methods as described in Example 2 below). 33% of control (non-IUD, no pharmacologic hormones) and 15% of IUD exposed endometria contained PTEN-null glands, a reduction of approximately 50% in the IUD group. Fisher exact test (two-tail) p=0.007. The results suggest that latent PTEN-null endometrial clones are reduced in prevalence in women treated with inert intrauterine devices. The magnitude of this effect is exactly concordant with that shown by epidemiologic studies of cancer outcomes in women using or not using inert IUDs.

TABLE 1

|  | Latent Precancer Absent (PTEN Normal) | Latent Precancer Present (PTEN null clone) | n |
|---|---|---|---|
| inert IUD | 67 (85%) | 12 (15%) | 79 (100%) |
| Control | 78 (67%) | 38 (33%) | 116 (100%) |
| Total | 145 | 50 | 195 |

Women with inert IUDs have an endometrial cancer risk of 0.37-0.61 times that of women without an IUD (Benshushan, et al., *Eur. J. Obstet. Gynecol. Reprod. Biol.* 105(2):166-169 (2002); and Hill, et al, *Int. J. Cancer* 70(3):278-281 (1997)). Combined with our observed 50% decline in the frequency of latent endometrial precancers in women using IUDs (Table 1), this IUD data suggests that a decline in endometrial latent precancer prevalence proportionately parallels reduced risk of clinical cancer outcome. Because latent precancers are common, and can be measured reliably in a single endometrial sample, measurement of significant alteration in their prevalence can be accomplished quickly in modest sized study populations. Involution of latent PTEN mutant clones is proposed as the mechanism of action of cancer risk reduction. The physiological effects of intrauterine device placement are mediated through a combination of mechanical and induced inflammatory factors. We conclude that augmentation of an inert IUD with impregnated inflammatory factors would increase the magnitude of latent precancer suppression.

Example 2

Magnitude of IUD-Induced Involution of PTEN-Mutant Endometrial Clones Increases with IUDs Impregnated with Drugs (Progestins) that Negatively Select for PTEN-Mutant Cells (Abbreviated as P-IUD)

The present Example describes experiments in which peri and postmenopausal women had an intake endometrial biopsy and underwent hormonal therapy with progestin-impregnated intrauterine device ("P-IUD," n=21, Mirena Coil, Phillips, et al., *J. Clin. Pathol.* 56(4):305-307 (2003)), cyclic oral progestins (n=28), or surveillance only (n=22), with follow-up biopsies. For comparison, premenopausal naturally cycling endometrial biopsies were studied as single time points in 87 patients, and multiple surveillance time points in 34. Biopsies in which any PTEN protein null glands were found by immunohistochemistry were scored as containing a latent endometrial precancer. All groups had a similar proportion of latent precancers at intake, but differed after therapy. Emergence rates of newly formed latent precancers were highest (21%) for the naturally cycling premenopausal group, in comparison to just 9% for untreated perimenopausal women. The progestin impregnated IUD group had the highest rate of latent precancer regression, with a 62% pre and 5% post therapy rate of latent precancers. This contrasted to non-significant changes for the low dose oral progestin and untreated control groups. We conclude that delivery of high doses of progestins locally to the endometrium by IUD leads to ablation of pre-existing PTEN-inactivated endometrial latent precancers, and is a possible mechanism for reduction of long term endometrial cancer risk known to occur in response to this hormone.

Materials and Methods

Patient Selection

Women in Northern Norway (Tromso region) with successive endometrial biopsies taken under different hormonal conditions form the three main experimental groups of this study. Clinical aspects of these patients have been published elsewhere (Vereide, et al., *Gynecol Oncol* 91:526-33 (2003)), but will be summarized here. Patients presenting with symptomatic endometrial bleeding and a diagnosis of endometrial hyperplasia had an intake endometrial biopsy followed by treatment either with a progestin impregnated intrauterine device (Group 1, P-IUD releasing 20 micrograms of levonorgestrel per day (Levonova device, Schering, Turku, Finland) or systemic oral progestin (Group 2, medroxyprogesterone 10 mg) administered daily for 10 days a month and repeated for 3 months. Patients were rebiopsied after receiving therapy. A comparison group (Group 3) of women with successive biopsies undergoing clinical surveillance for management of perimenopausal symptoms constituted a progestin "untreated" group from the same patient population. Just under half (10 of 22 reported in results) received low dose hormonal replacement therapy as follows: norestrin 1 mg/estradiol 2mg daily (6 patients), estriol 1-2mg daily (3 patients), tibolone 2.5 mg daily (1 patient), no therapy (12 patients). All patient materials were compiled from existing pathologic tissues generated as part of routine patient care ("discarded materials"), except for the P-IUD group, which was consented in advance.

Two additional groups of untreated patients were assembled for comparison. From Norway, pathology report and medical record review identified histologically normal proliferative endometrial biopsies from endogenously cycling premenopausal women without a recent or concurrent history of supplemental hormone use (Group 4). These were available only as single biopsies, without multiple sample points over time. Second, data from repeat biopsies of histologically normal proliferative endometrium of premenopausal endogenously cycling women in Boston, USA (Group 5) were made available for comparison from the original study that established baseline long-term persistence rates of morphologically unremarkable PTEN-null clones in normal cycling endometrium (Mutter, et al., *Cancer Res* 61:4311-4 (2001)).

Pathology Materials

Pre and post-treatment archival paraffin embedded blocks containing endometrial biopsy tissue were available for 26 P-IUD treated, 30 oral progestin treated, and 28 untreated control patients and single blocks from 99 proliferative reference patients. Of these, 22 were rejected because of inadequate amounts of endometrial tissue to perform immunohistochemistry, 1 control because of active progestin implant (Implanon) treatment, and 8 were rejected because of high background or other artifact during PTEN immunohistochemistry itself. This left paired biopsies from 21 P-IUD treated, 28 oral progestin treated, and 22 untreated control patients and single blocks from 87 proliferative reference patients for whom complete diagnostic and immunohistochemical results are available and reported in the results section.

Pathologist Diagnostic Review Using EIN Criteria

Slides were diagnosed according to EIN terminology by a gynecologic pathologist (GM) using published criteria. Endometria diagnosed as anovulatory had proliferative glands with focal cystic dilatation or branching, with or without associated vascular thrombi and stromal breakdown. Endometrial polyps are localizing lesions that met at least two of the following three diagnostic criteria in an area confirmed to be endometrial functionalis; 1) irregular gland architecture, 2) altered stroma; 3) thick walled vessels. Areas diagnosed as EIN were required to meet four criteria: 1) Area of glands exceeds area of stroma; 2) when a localizing lesion is present, epithelial cells within the architecturally crowded focus was cytologically different compared to background; 3) area meeting architectural and cytologic criteria must have a minimum size of 1 mm; 4) exclusion of mimics and carcinoma.

PTEN Immunohistochemistry

Paraffin sections of endometrial biopsy and curetting specimens were rehydrated, and underwent antigen retrieval by microwave before overnight (4° C.) incubation with 1:300 murine monoclonal anti-PTEN antibody 6h2.1 (Cascade Biosciences, Winchester, Mass.) as previously described (Mutter, et al, *Cancer Res* 61:43114 (2001)). Slides were washed, and incubated with appropriate secondary biotinylated immunoglobulin (Vectastain ABC kit, Vector Laboratories, Inc., Burlingame, Calif.) and signal detected by sequential addition of avidin peroxidase and 3,3'-diaminobenzidine. Slides were counterstained by methyl-green and coverslipped.

Each block underwent PTEN staining in independent duplicate immunohistochemical runs that included standard known slides as a run quality control. Staining adequacy was assessed by internal positive control staining in the slide of interest (normal endometrial stroma), a negative control of each slide in which primary antibody had been omitted, and review of run controls. PTEN status was scored visually (by GLM) as "PTEN null" if any endometrial glands devoid of PTEN protein were seen, and "PTEN normal" if all endometrial glands visualized expressed PTEN protein.

Data Reduction

Data were entered into an excel spreadsheet which was imported into Systat (version 11, Systat Software, Inc., Point Richmond, Calif.) for statistical analysis.

Results

Clinical and demographic characteristics of all patient groups are shown in Table 2. Histologic diagnosis of intake biopsies is shown in Table 3.

Patient age was similar within the separate perimenopausal (Groups 1-3, average 48-53 years) and premenopausal (Groups 4-5, average 41-42 years) groups, but as expected, differ between them (ANOVA p<0.001). Using all 192 patients reported in this study, we tested whether there was a correlation between decade of age at time of first available biopsy and the PTEN status of that biopsy. The proportion of PTEN-null glands at initial presentation did increase steadily with decade of age from a low of 32% in women less than 30 years old, to a high of 53% in women over 50, but the magnitude of the effect was not significant (Cochran's Test of Linear Trend, p=0.522).

The prevalence of latent precancers at initial presentation (no treatment) was similar between all five groups studied (Chi-Square p=0.077). The proportion of latent precancers in follow-up biopsies, however, showed significant differences between the 4 available groups(Chi-Square p=0.002), suggesting a possible effect of intervention.

Sequential sampling before and after treatment provided an initial reference point (pre-treatment) to determine the overall magnitude and significance of a post-treatment effect. This was analyzed by pre and post therapy group comparison of latent precancer proportions (Table 4). The only group which showed a significant change overall in the proportion of PTEN-null endometria over time is the P-IUD treated patients (Fishers exact p<0.001). 62% of pre-treatment endometria contained PTEN null glands, declining to only 5% after an average of 49 days of treatment with the progestin impregnated IUD.

The pattern of change in latent precancers in paired samples over time in individual patients provides some insights into the balance of PTEN-null gland emergence, persistence, and regression events within each treatment group (Table 5). 29-50% of patients in each group had no PTEN-null clones at any time during the study. Those patients who had a minimum of one biopsy with a latent precancer were classified as: 1) emergent, when only the second biopsy contained a latent precancer, 2) persistent, when both the first and second samples has a latent precancer, and 3) regressed, when a latent precancer seen in the first biopsy was absent in the second. Highest regression rates were seen in the P-IUD group, where 62% of all patients had a latent precancer at intake, and all of these regressed by the second biopsy (chi square p<0.001). Highest emergence rates were seen in the (untreated) groups of normal endogenously cycling proliferative endometria (Group 5, PE2), where 21% of all patients developed a new latent precancer during follow-up, but this was not statistically significant (chi square p=0.1 16). Persistence rates were highest in the endogenously cycling proliferative endometria (29%), and the cyclical low dose oral progestin perimenopausal (35.7) group (chi square p=0.006).

TABLE 2

| | | | Clinical characteristics of patient groups | | | |
|---|---|---|---|---|---|---|
| Group # | Group Name | n | Treatment | Biopsies | Site | Age, mean (median)/range |
| 1 | P-IUD | 21 | progestin-impregnated IUD | pre-post | Norway | 49 (50)/33-62 |
| 2 | p-cycle | 28 | cyclic oral medroxyprogesterone | pre-post | Norway | 48 (49)/32-58 |
| 3 | Control | 22 | perimenopause surveillance | sequential | Norway | 53 (51)/37-93 |

TABLE 2-continued

Clinical characteristics of patient groups

| Group # | Group Name | n | Treatment | Biopsies | Site | Age, mean (median)/range |
|---|---|---|---|---|---|---|
| 4 | PE1 | 87 | normal proliferative, endogenous cycle | single | Norway | 42 (43)/29-52 |
| 5 | PE2 | 34 | normal proliferative, endogenous cycle | sequential | Boston | 41 (42)/24-52 |

TABLE 3

Intake endometrial histopathology of patient groups

| Pathology Diagnosis | Group 1 P-IUD | Group 2 p-cycle | Group 3 Control | Group 4 PE1 | Group 5 PE2 | Total |
|---|---|---|---|---|---|---|
| Benign | 8 | 9 | 10 | 87 | 34 | 148 |
| EIN | 1 | 2 | 1 | 0 | 0 | 4 |
| Endometrial Polyp | 3 | 1 | 0 | 0 | 0 | 4 |
| Unopposed estrogen effect | 9 | 16 | 11 | 0 | 0 | 36 |
| Total | 21 | 28 | 22 | 87 | 34 | 192 |

TABLE 4

Prevalence of PTEN-null endometria by groups

| Group # | Group Name | n | Pre-Rx % (n) | Post-Rx % (n) | Interval, mean (median)/range | p, (Fisher exact) unpaired |
|---|---|---|---|---|---|---|
| 1 | P-IUD | 21 | 62 (13) | 5 (1) | 251 (164)/38-1142 | <0.001 |
| 2 | p-cycle | 28 | 68 (19) | 39 (11) | 332 (154)/38-1248 | 0.060 |
| 3 | Control | 22 | 41 (9) | 18 (4) | 442 (252)/43-1601 | 0.185 |
| 4 | PE1 | 87 | 49 (43) | nd | 0 | nd |
| 5 | PE2 | 34 | 35 (12) | 50 (17) | 401 (400)/26-1167 | 0.327 |
| Totals | | | 50 (96/192) | 31 (33/105) | | |
| Chi-square | | | p = 0.077 | p = 0.002 | | |

TABLE 5

Latent precancer absence, emergence, persistence, and regression in successive samples of individual patients

| Group # | Group Name | n | Absence absent→absent % (n) | Emergence absent→present % (n) | Persistence present→present % (n) | Regression present→absent % (n) |
|---|---|---|---|---|---|---|
| 1 | P-IUD | 21 | 33.3 (7) | 4.8 (1) | 0.0 (0) | 61.9 (13) |
| 2 | p-cycle | 28 | 28.6 (8) | 3.6 (1) | 35.7 (10) | 32.1 (9) |
| 3 | Control | 22 | 50.0 (11) | 9.1 (2) | 9.1 (2) | 31.8 (7) |
| 5 | PE2 | 34 | 44.1 (15) | 20.6 (7) | 29.4 (10) | 5.9 (2) |
| Total | Total | 105 | 39.0 (41) | 10.5 (11) | 21.0 (22) | 29.5 (31) |
| | Pearson chi-sq | | 0.383 | 0.116 | 0.006 | <0.001 |

Each patient was classified based upon changes in latent precancer occurrence over time (absent or present, shown for first→second timepoints). For each group (row), the percentage of patients with latent precancers having a pattern of absence, emergence, persistence, or regression is shown.

Discussion

Changes in endometrial latent precancer rates, as detected by PTEN immunohistochemistry, were studied in untreated controls, and women either taking cyclic low dose oral progestins or having placement of a progestin impregnated IUD. All groups initially had comparable proportions of patients whose endometria contained PTEN null-glands, but these diverged significantly after therapy. The progestin impregnated IUD group, which delivered the highest local dose of progestins for the longest period, experienced a strong trend towards regression of pre-existing latent precancers, with all latent precancers seen at intake disappearing on post-therapy follow-up. Involution rates were modest and statistically insignificant for the other treatment and control groups.

Progestins are capable of inducing dose dependent apoptotic cell death of neoplastic endometrial cells grown in culture, but with a rapid extinction over a period of a few days. Subsequent withdrawal is accompanied by resumption of apoptotic cell death on a scale several orders of magnitude greater than achieved in the preceding steady state. Dose and schedule of administration therefore interact in defining the net effect. Local delivery of progestins by placement of an impregnated intrauterine device provides a very high endometrial concentration of hormone while diminishing the complications of systemic distribution. Such devices have even been effective in treatment of established well differentiated endometrial adenocarcinoma (Montz, et al., *Am. J. Obstet. Gynecol.* 186(4):651-657 (2002)) and present non-surgical alternative therapies for management of premalignant endometrial lesions.

Declines in pre-existing latent precancers were not seen in endogenously driven normal menstrual cycles, and cyclic oral administration of low dose progestins. It is entirely possible that the cancer protective effects seen in low dose oral progestin and combination contraceptive administration require a longer duration to achieve than the relatively short term follow-up in this study. There was a measurable, but not statistically significant difference, however, in the emergence of new latent precancers during follow-up between these groups, with 21% of all cycling proliferative patients developing emergent latent precancers during follow-up, compared to only 4-9% in the more quiescent endometria of the three perimenopausal groups (Groups 1,2,3). This is no surprise as random mutagenesis, the presumed mechanism of origin for most latent precancers, is expected to occur in proportion to the mitotic activity of the source tissue.

Despite a high rate of acquired PTEN mutation in histologically normal tissues, and a correspondingly low lifetime incidence of endometrial cancer, there are good reasons to link inactivation of PTEN to endometrial carcinogenesis. PTEN knockout mice develop endometrial carcinoma in 20% of cases (Stambolic, et al., *Cancer Res.* 60:3605-11 (2000)). PTEN mutation is the most common genetic defect in endometrioid endometrial adenocarcinomas. Carry-forward of exact PTEN mutations seen in precancers to subsequent cancers in the same patient establishes lineage continuity between premalignant and malignant phases of disease (Mutter, et al., *J. Nat'l Cancer Inst.* 92:924-30 (2000)). Loss of PTEN tumor suppressor functions including Akt-dependent enabling of apoptosis and control of cell division rates, confer proliferative and survival advantages long associated with the neoplastic phenotype (Mutter, *Am. J. Pathol.* 158:1895-8 (2001)).

All references cited herein are fully incorporated by reference. Having now fully described the invention, it will be understood by those of skill in the art that the invention may be practiced within a wide and equivalent range of conditions, parameters and the like, without affecting the spirit or scope of the invention or any embodiment thereof.

What is claimed is:

1. A method of preventing the development of endometrial cancer in a woman comprising:
    a) identifying said woman as being at increased risk of developing endometrial cancer;
    b) implanting an intrauterine device in the woman identified in step a) wherein said intrauterine device releases an inflammatory cytokine.

2. The method of claim 1, wherein said inflammatory cytokine is selected from the group consisting of: LIF; OSM; and CNTF.

3. The method of claim 1, wherein said inflammatory cytokine is selected from the group consisting of MIP-1α; MIP-1β; MCP-1; MCP-2; MCP-3; RANTES; and lymphotactin.

4. The method of claim 1, wherein the risk of said woman developing endometrial cancer is determined by assaying a sample of endometrial cells obtained from said woman for PTEN expression or activity.

5. The method of claim 1, wherein said woman does not have a history of endometrial cancer and does not exhibit uterine endometrial cell hyperplasia.

6. The method of claim 1, wherein said IUD releases 0.01-100 μg of inflammatory cytokine over a 24 hour period.

7. The method of claim 1, wherein said inflammatory cytokine is IL-1.

8. The method of claim 1, wherein said inflammatory cytokine is IL-6.

9. The method of claim 1, wherein said inflammatory cytokine is IL-11.

10. The method of claim 1, wherein said inflammatory cytokine is TNF-α.

11. The method of claim 1, wherein said inflammatory cytokine is TNF-β.

12. The method of claim 1, wherein said inflammatory cytokine is IFN-α.

13. The method of claim 1, wherein said inflammatory cytokine is IFN-β.

14. The method of claim 1, wherein said inflammatory cytokine is IFN-γ.

15. The method of claim 1, wherein said inflammatory cytokine is IL-8.

16. The method of claim 1, wherein said inflammatory cytokine is IL-12.

17. The method of claim 1, wherein said inflammatory cytokine is PF-4.

18. The method of claim 1, wherein said inflammatory cytokine is PBP.

19. The method of claim 1, wherein said inflammatory cytokine is NAP-2.

20. The method of claim 1, wherein said inflammatory cytokine is β-TG.

* * * * *